(12) United States Patent
Han et al.

(10) Patent No.: US 9,332,969 B2
(45) Date of Patent: May 10, 2016

(54) FLUID FLOW CONTROL APPARATUS AND PATIENT FLUID SAMPLING METHOD

(75) Inventors: Steve Han, Upland, CA (US); Alex Stenzler, Long Beach, CA (US)

(73) Assignee: CareFusion 207, Inc., San Diego, CA (US)

(*) Notice: Subject to any disclaimer, the term of this patent is extended or adjusted under 35 U.S.C. 154(b) by 845 days.

(21) Appl. No.: 12/349,118

(22) Filed: Jan. 6, 2009

(65) Prior Publication Data
US 2010/0174210 A1 Jul. 8, 2010

(51) Int. Cl.
| | |
|---|---|
| A61C 17/06 | (2006.01) |
| A61C 17/14 | (2006.01) |
| A61M 1/00 | (2006.01) |
| F16K 11/085 | (2006.01) |
| E03B 7/07 | (2006.01) |
| F16K 37/00 | (2006.01) |
| F17D 3/00 | (2006.01) |
| A61B 5/00 | (2006.01) |
| B65D 81/00 | (2006.01) |
| A61B 10/00 | (2006.01) |

(Continued)

(52) U.S. Cl.
CPC ......... *A61B 10/0096* (2013.01); *A61B 10/0045* (2013.01); *A61M 1/0001* (2013.01); *A61M 39/223* (2013.01); *A61M 2039/229* (2013.01); *F16K 11/083* (2013.01)

(58) Field of Classification Search
CPC ............ A61M 39/223; A61M 1/0001; A61M 2039/229; F16K 11/083
USPC ........ 137/556, 556.6, 553, 15.24, 15.21, 268, 137/625.47; 604/30, 31, 32, 167.05, 248, 604/246, 23, 35, 93.01, 118, 119; 239/59; 433/92, 95, 97; 210/320, 801, 521, 210/532.1; 251/312; 600/579, 575, 573
See application file for complete search history.

(56) References Cited

U.S. PATENT DOCUMENTS 172,568 A * 1/1876 Hughes ..................... 137/625.47
3,276,472 A * 10/1966 Jinkens et al. ................ 137/556

(Continued)

FOREIGN PATENT DOCUMENTS

| CN | 101011270 A | 8/2007 |
|---|---|---|
| CN | 101179999 A | 5/2008 |

(Continued)

OTHER PUBLICATIONS

PCT Search Report (mailed Apr. 6, 2010); 17 pgs.

(Continued)

*Primary Examiner* — Mary McManmon
*Assistant Examiner* — Hailey K Do
(74) *Attorney, Agent, or Firm* — McDermott Will & Emery LLP

(57) ABSTRACT

A fluid flow control apparatus used in medical fluid sampling. The apparatus includes a valve assembly, first and second ports, and a cap. The valve assembly comprises a body rotatably assembled to a housing and defining a passageway and at least two recesses defined by an interior surface of the housing and the body which is formed separate from the passageway. The ports extend from the housing and are configured for connection to medical devices. The valve assembly is operable to interchangeably align the passageway and the recesses with the ports. Finally, the cap is connected to the housing, and forms an opening for coupling to a specimen container.

16 Claims, 11 Drawing Sheets

(51) Int. Cl.
  *A61M 39/22* (2006.01)
  *F16K 11/083* (2006.01)

(56) References Cited

U.S. PATENT DOCUMENTS

| | | | |
|---|---|---|---|
| 3,674,052 A | | 7/1972 | Hartman et al. |
| 3,833,000 A | | 9/1974 | Bridgman |
| 3,855,997 A | | 12/1974 | Sauer |
| 3,907,688 A | * | 9/1975 | Close .......................... 210/424 |
| 4,219,021 A | * | 8/1980 | Fink .......................... 137/556.6 |
| 4,273,126 A | | 6/1981 | Grane et al. |
| 4,332,560 A | * | 6/1982 | Rait ................................ 433/92 |
| 4,397,335 A | * | 8/1983 | Doblar et al. ............ 137/625.19 |
| 4,569,344 A | | 2/1986 | Palmer |
| 4,729,401 A | | 3/1988 | Raines |
| 4,740,202 A | | 4/1988 | Stacey et al. |
| 4,915,691 A | | 4/1990 | Jones et al. |
| 5,045,077 A | | 9/1991 | Blake, III |
| 5,122,129 A | * | 6/1992 | Olson et al. .................. 604/240 |
| 5,158,569 A | | 10/1992 | Strickland et al. |
| 5,237,993 A | | 8/1993 | Skrabal |
| 5,334,163 A | | 8/1994 | Sinnett |
| 5,376,071 A | | 12/1994 | Henderson |
| 5,474,526 A | * | 12/1995 | Danielson et al. ............. 604/6.1 |
| 5,792,126 A | | 8/1998 | Tribastone et al. |
| 5,865,812 A | | 2/1999 | Correia |
| 6,375,625 B1 | | 4/2002 | French et al. |
| 6,379,340 B1 | | 4/2002 | Zinger et al. |
| 6,457,488 B2 | | 10/2002 | Loo |
| 6,536,742 B2 | * | 3/2003 | Lotz et al. ..................... 251/297 |
| 6,592,769 B1 | * | 7/2003 | Erickson ...................... 210/801 |
| D483,487 S | | 12/2003 | Harding et al. |
| 6,890,323 B1 | | 5/2005 | Antonelli |
| 2002/0017328 A1 | * | 2/2002 | Loo .......................... 137/625.47 |
| 2004/0210162 A1 | * | 10/2004 | Wyatt et al. ................... 600/573 |
| 2005/0199237 A1 | | 9/2005 | Lurie |
| 2008/0067462 A1 | | 3/2008 | Miller et al. |
| 2010/0174210 A1 | | 7/2010 | Han et al. |

FOREIGN PATENT DOCUMENTS

| | | |
|---|---|---|
| DE | 39 12 257 A1 | 10/1990 |
| EP | 1 459 783 A1 | 9/2004 |
| JP | S54087794 U | 7/1979 |
| JP | S63-285375 A | 11/1988 |
| JP | 2674719 B | 9/1994 |
| JP | H08-500763 A | 1/1996 |
| JP | H09229828 | 9/1997 |
| JP | 2001140723 A | 5/2001 |
| JP | 2003033441 A | 2/2003 |
| JP | 2004353845 A | 12/2004 |
| JP | 2005287681 A | 10/2005 |
| RU | 2000817 C1 | 10/1993 |
| RU | 26003 U1 | 11/2002 |
| SU | 506394 A1 | 3/1976 |
| SU | 1644969 A1 | 4/1991 |

OTHER PUBLICATIONS

Russian Office Action, Russian Application No. 2011133083, dated Dec. 5, 2013, pp. 1-3.
Japanese Office Action, Japanese Application No. 2011-544497, dated Feb. 25, 2014 (7 pages).
Australian Examination Report No. 1 for Australian Application No. 2009335668, dated Sep. 17, 2014, 4 pages.
European Office Action for European Application No. 09775522.7, dated Nov. 22, 2013, 4 pages.
First Chinese Office Action for Chinese Application No. 200980153895.X, dated Jan. 14, 2013, 12 pages.
Japanese Decision to Grant for Japanese Application No. 2011-544497, dated Sep. 24, 2014, 3 pages (translation unavailable).
Mexican Office Action for Mexican Application No. MX/a/2011/007286, 6 pages.
Notification to Grant Patent Right for Invention for Chinese Application No. 200980153895.X, dated Jul. 31, 2013, 4 pages.
Russian Decision on Grant for Russian Application No. 2011133083/14, 13 pages.
Australian Examination Report No. 2 for Application No. 2009335668, dated Sep. 2, 2015, 4 pages.
Australian Examination Report No. 3 for Application No. 2009335668, dated Sep. 16, 2015, 5 pages.
Korean Office Action for Application No. 10-2011-7018378, dated Sep. 21, 2015, 9 pages.
European Intention to Grant for Application No. 09775522.7, dated Jun. 16, 2015, 32 pages.

* cited by examiner

FLUID FLOW CONTROL APPARATUS AND PATIENT FLUID SAMPLING METHOD

BACKGROUND

The present disclosure relates generally to patient specimen collection devices. More particularly, it relates to devices for collecting fluid samples from a patient's respiratory system and incorporating a fluid flow control apparatus having aspiration and instillation capabilities without a loss of internal pressure.

Fluid sampling devices are commonly used to collect fluid samples from a patient's airway or other body cavities. The fluid sample may be subjected to laboratory testing or evaluation, therefore the integrity of the sample must be maintained during the sampling procedures. Additionally, it is often necessary to avoid secondary infection or contamination of other persons during the sampling procedure. With some sampling techniques, a fluid is instilled into a patient's airway or other body cavity (e.g., via an intubated catheter), and then aspirated back (along with a specimen from the targeted area) into a sampling container. The fluid sample is then directed into a collection container in order that the sample may be examined for cells, micro organisms, blood or other biological material. To assist in these efforts, a fluid flow control apparatus can be employed that enables the user to control the direction and/or amount of fluids transported in a given system or procedure. The majority of apparatuses used for this procedure are either separate apparatuses whereby, following instillation, the catheter or tube is exposed to room air and internal pressure is lost, or multiple stopcocks are required to accomplish the same functions.

In light of the above, needs exist for improved fluid flow control apparatuses used with patient fluid sampling devices and methods.

SUMMARY

One aspect provides a fluid flow control apparatus used in medical fluid sampling. The apparatus includes a valve assembly comprising a body that defines a passageway, the body rotatably assembled to a housing along an axis of rotation, and at least two recesses defined by an interior surface of the housing and the body that are is formed separate from the passageway. The apparatus further including a first port and a second port, each extending from the housing and configured for connection to medical devices. In this regard, valve assembly is operable to interchangeably align the passageway and the two recesses with the ports. Finally, the apparatus includes a cap connected to the housing that includes an opening for coupling to a specimen container.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
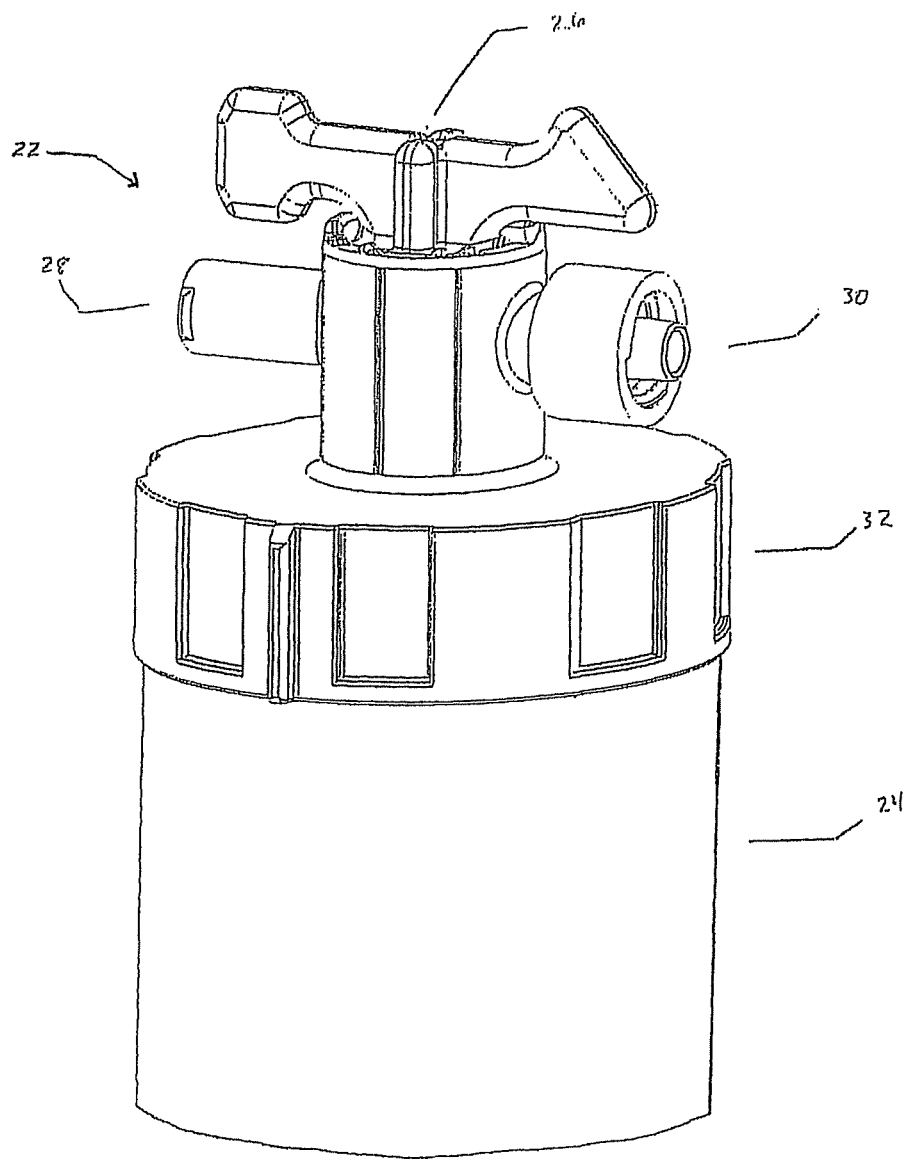
FIG. 1 is a side perspective view of a fluid sampling device according to aspects of the present disclosure.

One construction of a fluid sampling device 20 in accordance with the present disclosure is shown in FIG. 1 and includes a fluid flow control apparatus 22 and a specimen container 24. The fluid flow control apparatus 22 includes a valve assembly 26, first and second ports 28, 30, and a cap 32. Details on the various components are provided below. In general terms, however, the fluid flow control apparatus 22 is selectively secured to the specimen container 24. The valve assembly 26 operates to selectively fluidly connect the first and second ports 28, 30 with each other and the specimen container 24. With this construction, the fluid sampling device 20 can be employed to obtain respiratory fluid samples or specimens from an intubated patient as part of a patient ventilation system, such as in conjunction with a bronchoalveolar lavage procedure, by instillating liquid into, and aspirating fluid specimens from, the patient.

Figure 2:
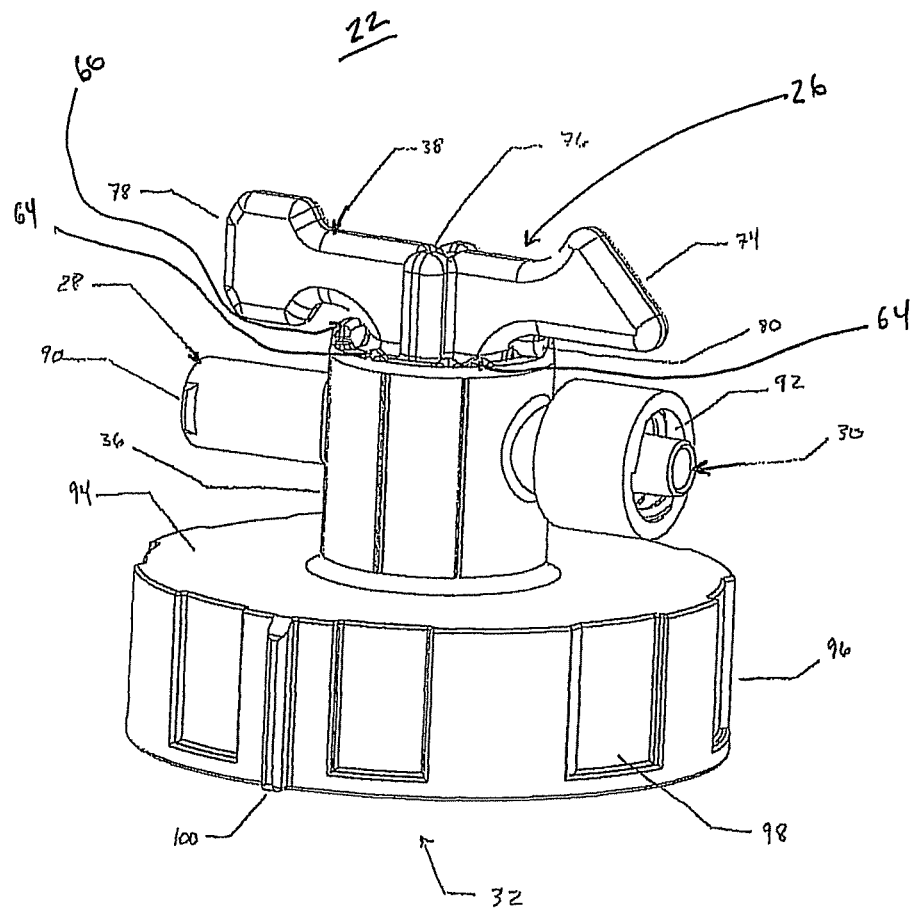
FIG. 2 is a side perspective view of a fluid flow control apparatus in accordance with aspects of the present disclosure and useful with the device of FIG. 1.
Figure 3:
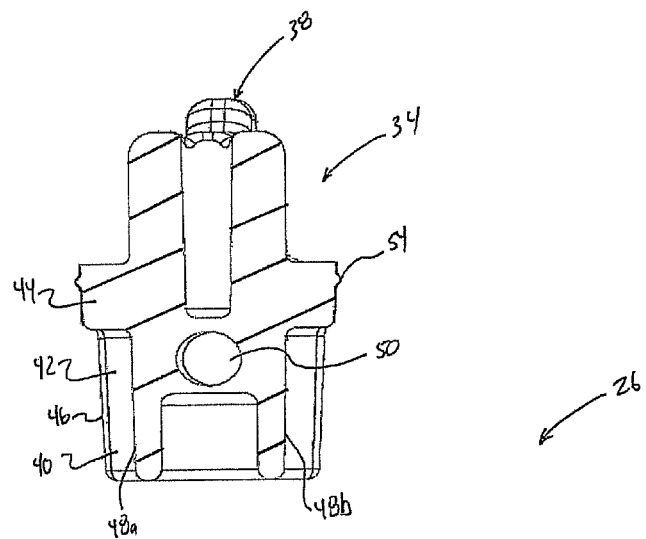
FIG. 3 is an exploded, cross-sectional view of the fluid flow control apparatus of FIG. 2.
Figure 3:
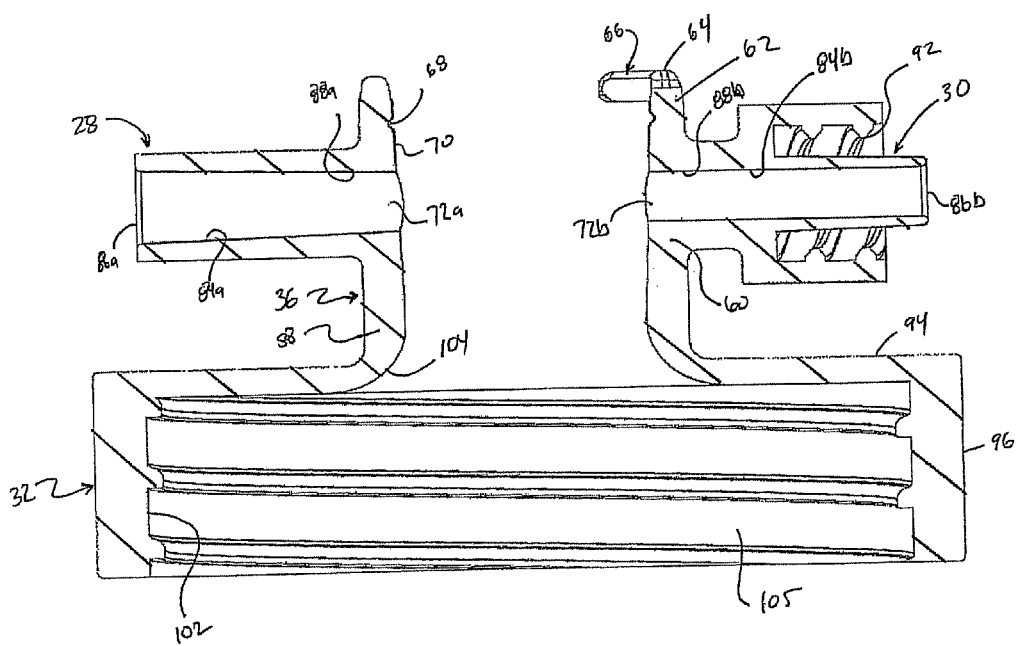

With reference to FIGS. 2 and 3, the valve assembly 26 includes a valve body 34, a housing 36, and a handle 38. The valve body 34 is rotatably maintained by the housing 36, with the handle 38 serving to allow a user to selectively alter a rotational position of the valve body 34 relative to the housing 36. The valve assembly 26 is configured as a stopcock valve in some embodiments, although ball, gate or other suitable valves may be used.

Figure 4A:
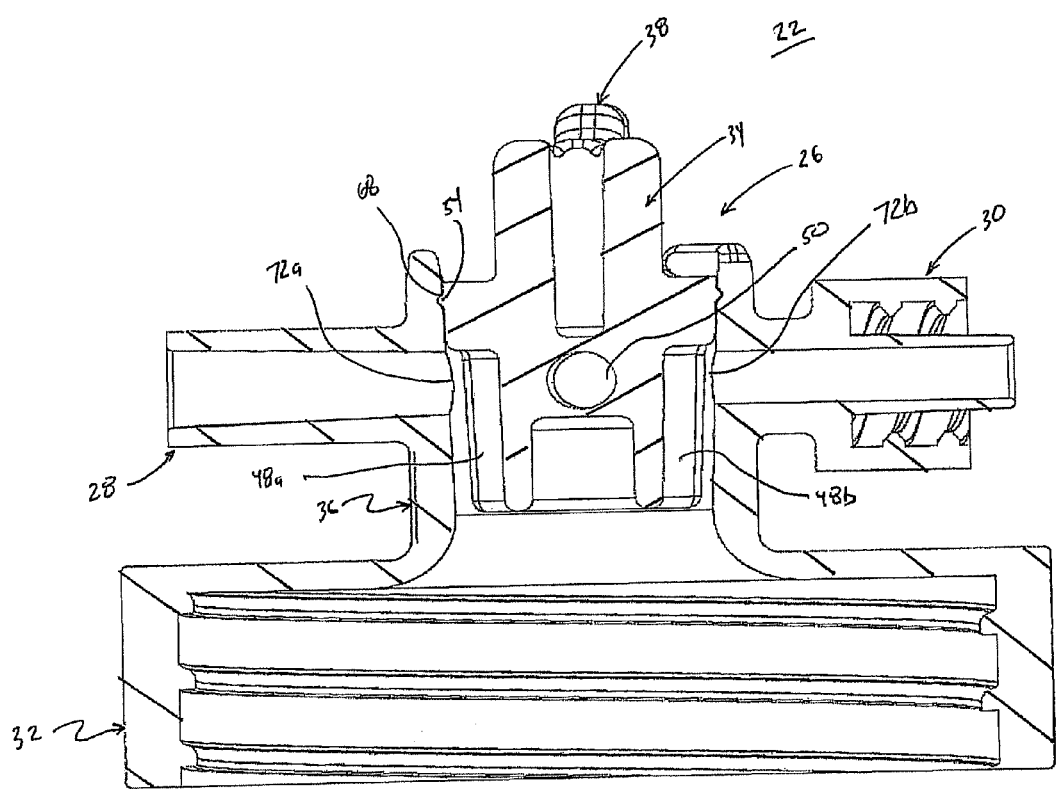
FIG. 4A is a cross-sectional view of the fluid flow control apparatus of FIG. 3 upon final assembly and in a first position.
Figure 4B:
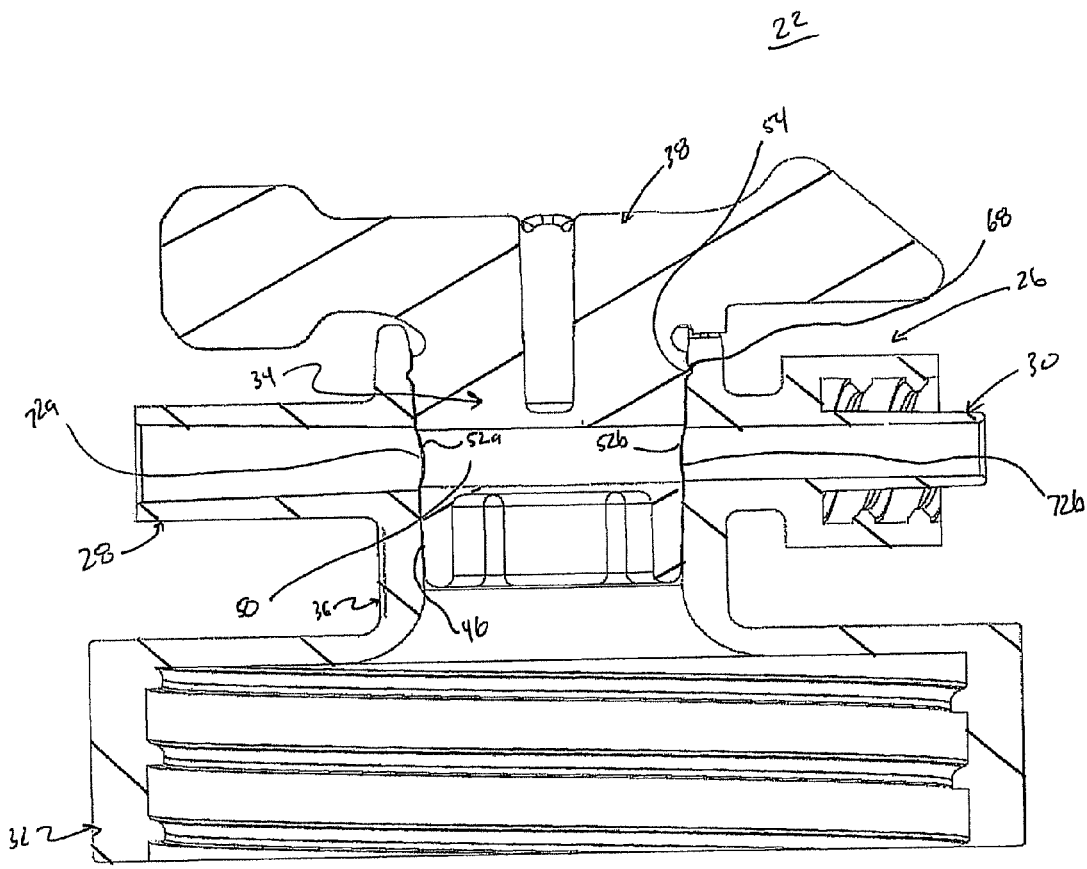
FIG. 4B is a cross-sectional view of the fluid flow control apparatus of FIG. 4B in a second position.

As illustrated in FIG. 3, the valve body 34 includes or forms a base 40, an intermediate section 42, and a stem 44. The base 40 has an exterior surface 46 along which opposing recesses or grooves 48a, 48b are defined. The intermediate section 42 extends from the base 40, and forms a passageway 50. The passageway 50 is fluidly open to an exterior of the intermediate section 42 at opposing, first and second ends 52a, 52b (best shown in FIG. 4B). As shown, the passageway 50 is fluidly isolated from the recesses 48a, 48b. Relative to the upright orientation of the valve assembly 26 shown, the passageway 50 can be described, in some embodiments, as being horizontal whereas the recesses 48a, 48b are vertical. Other constructions, however, are also acceptable. The stem 44 extends from the intermediate section 42 opposite the base 40, and in some embodiments forms a circumferential rib 54 configured for rotatable assembly to the housing 36, as described below.

The housing 36 is sized to receive the valve body 34, and can be integrally formed with the ports 28, 30 and the cap 32 as shown. Regardless, the housing 36 includes or forms a lower portion 58, an intermediate portion 60, and an upper portion 62. The upper portion 62 has a ridge 66 along which position indicators 64 are formed. The position indicators 64 are further illustrated in FIG. 2 and may be formed as touch-feel indicators or any other useful configuration. In one embodiment, the position indicators 64 project outward along the ridge 66 of the upper portion 62. The position indicators 64 may be selectively formed as raised points or as raised elongated sections. Alternatively, the position indicators 64 may be selectively formed as grooves or recesses in the ridge 66. The upper portion 62 also includes a channel 68 on an interior surface 70 of the housing 36. The channel 68 may continuously extend around the perimeter of the interior surface 70. The intermediate portion 60 extends from the upper portion 62, in a direction opposite the ridge 66, and forms opposing openings 72a, 72b. The lower portion 58 extends from the intermediate portion 60.

With reference to FIG. 2, the handle 38 includes a directional end 74, an opposing terminal end 78, and a midpoint 76. In some embodiments, the directional end 74 includes a tang 80. The tang 80 may be formed as a protrusion or extension on the directional end 74. The midpoint 76 defines an axis of rotation that extends through the handle 38 and valve body 34. The handle 38 can assume a variety of shapes conducive to convenient grasping by a user's hand/fingers.

Connection of the handle 38 with the valve body 34 is shown in FIGS. 2 and 3. The handle 38 provides a means for a medical personal to rotate the valve body 34 within the housing 36 of the valve assembly 26. The handle 38 is aligned with the passageway 50 (i.e., a direction of extension of the handle 38 between the ends 74, 78 corresponds with an axis of the passageway 50); in this manner, the orientation of the handle 38 provides confirmation to a user in aligning the passageway 50 relative to the ports 28, 30. A relationship of the tang 80 of the handle 38 and the position indicators 64 is further reflected in the view of FIG. 2. The tang 80 of the handle 38 interacts with the position indicators 64 on the ridge 66 on the upper portion 62 of the housing 36 as the handle 38 is turned. In one embodiment, the position indicator 64 consists of a pair of closely positioned molded protrusions, formed such that the tang 80 may rest comfortably between the protrusions and may also move past them. In one embodiment, the position indicators 64 may also be formed to prevent further rotation of the handle 38 in a certain direction by protruding a sufficient distance above the ridge 66 to interfere with further movement of the tang 80 in that direction. Generally, the positions of the position indicators 64 correspond to the desired positions of the valve body 34 useful in patient fluid sampling.

The valve body 34 rotates within the housing 36 of the valve assembly 26. The housing 36 is configured to enclose the working components of the valve body 34. A relationship of the channel 68 of the housing 36 and the rib 54 of the valve body 34 is further reflected in the views of FIGS. 4A and 4B. As shown, the channel 68 serves as a path within which the rib 54 rotates and serves to rotatably secure the valve body 34 within the housing 36. The rib 54/channel 68 interface is configured to provide a consistent, long term seal and leak tight fit. The exterior surface 46 of the valve body 34 maintains a fluidly sealed relationship with the interior surface 70 of the housing 36. Other mounting relationships of the valve body 34 within the housing 36 are also equally acceptable. The passageway 50 and recesses 48a, 48b are sized and defined within the valve body 34 such that they correspond with openings 72a, 72b when aligned. For example, in the first valve body position of FIG. 4A, the recesses 48a, 48b are aligned with the openings 72a, 72b of the housing 36. In the second valve body position of FIG. 4B, the openings 72a, 72b of the housing 36 are aligned with the passageway 50 of the valve body 34 through reorientation of the valve body 34 when the handle 38 is turned (i.e., transitioned from the position or state of FIG. 4A to the position or state of FIG. 4B).

Returning to FIG. 1, it is illustrated that the first and second ports 28, 30 are attached to the valve assembly 26, mounted substantially opposite one another along the housing 36. The ports 28, 30 can be integrally formed with or by the housing 36. Alternatively, the ports 28, 30 can be formed separately and later assembled to the housing 26. Further illustrated in FIG. 3, the ports 28, 30 are structural bodies forming passageway 84a, 84b with inlet ends 86a, 86b and outlet ends 88a, 88b, respectively. The inlet end 86a of the port 28 may be formed with exterior barbs 90, as shown in FIG. 2. The inlet end 86b of the port 30 may be formed recessed threading 92. The ports 28, 30 may be female and male fittings and additionally may be luer fittings or any other suitable fitting type. To this end, the second port 30 is suitable for connection to a catheter or other tube or apparatus suitable for placement and connection within a patient's bodily cavity (e.g., lung) or organ. The first port 28 is suitable to connect and disconnect to various medial devices without removal of the catheter (or other component) from the second port 30. In more general terms, however, the ports 28, 30 are configured to facilitate coupling with a flexible tube, catheter or other medical device which can be received, and connection maintained, with the ports 28, 30.

Figure 5:
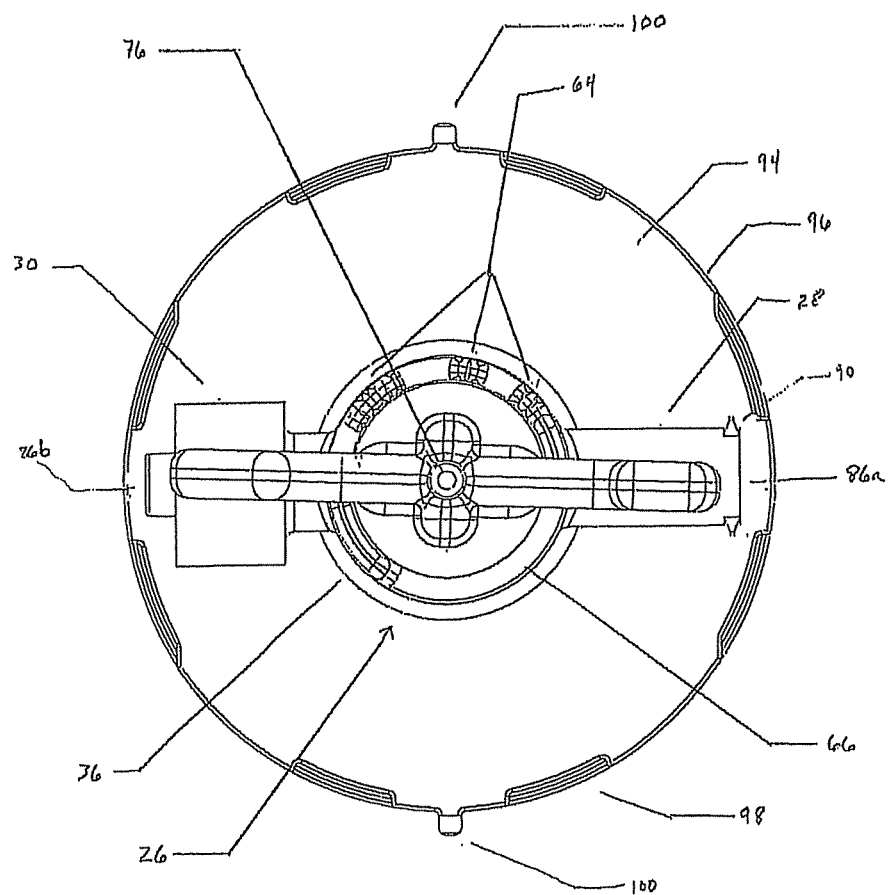
FIG. 5 is a top view of the fluid flow control apparatus of FIG. 2.

As illustrated in FIGS. 3 and 5, the cap 32 includes a top 94 and a perimeter 96 extending from the top 94 of the cap 32 at a length necessary to provide sealable engagement with the fluid sampling container 24 (FIG. 1) as described below. In one embodiment, the perimeter 96 includes indentations 98 for ease of handling by medical personnel. Additionally, the perimeter 96 may include flanges 100 to assist with handling. The perimeter 96 also includes a threaded interior surface 102 that correspond with a threaded exterior (not shown) of the fluid sampling container 24, although other assembly techniques (e.g., snap-fit) are also acceptable. Regardless, the top 94 forms an opening 104 through which a fluid connection between an interior of the housing 36 and a chamber 105 of the cap 32 is established. The cap 32 may be constructed of the same material as the housing 36, or other suitably compatible material. The cap 32 may be formed integrally with the housing 36, or attached later in the production process of the fluid flow control apparatus 22.

With the above construction, the valve assembly 26 is sealed into the cap 32 such that the passageway 50 of the valve assembly 26 can be oriented and fluidly connected to the cap 32 as needed for the desired medical procedure. With this in mind, the opening 104 of the cap 32 has a diameter corresponding with the dimensional attributes of the interior surface 70 of the housing 36 to ensure a desired arrangement of the valve body 34 relative to the cap 32 upon final assembly. Further, additional components useful in establishing and maintaining the desired fluid connection, such as a coupling, a seal, etc. may be included. The valve assembly 26 may also be either formed integrally with, or appropriately sealed, to the ports 28, 30.

Returning to FIG. 1, the specimen container 24 may be any standard container used for specimen sampling purposes. In one embodiment, the specimen container 24 may be clear or translucent in color and may also include volume indicators along the side. The specimen container 24 may be constructed of a plastic or any other suitable material. Although not shown, container 24 includes a threaded exterior portion that selectively engages with the threaded interior surface 102 (FIG. 3) of the cap 32 for a sealed connection.

The fluid sampling device 20 includes the valve assembly 26 with at least two positions, and may include four positions, to facilitate sampling of a patient's fluids. To this extent, the position indicators 64 (FIG. 2) may consist of point positions, for example when the valve assembly 26 is in an aspiration or instillation position, or elongated indicators as when the valve assembly 26 is in a sealed position.

Figure 6:
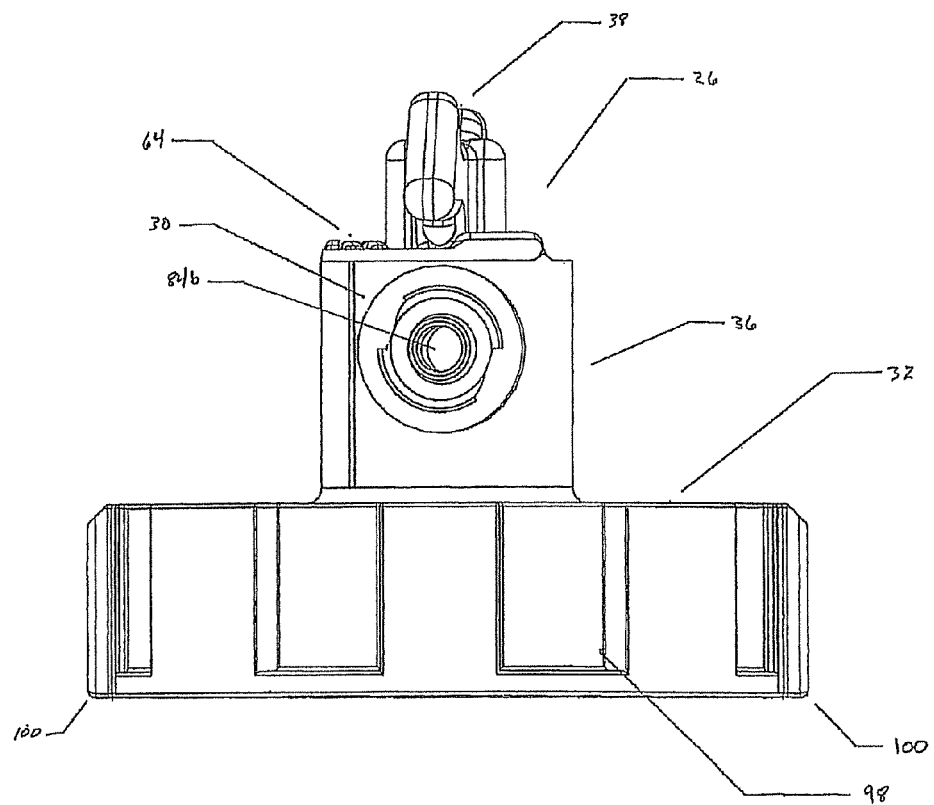
FIG. 6 is a front view of the fluid sampling device of FIG. 1 in an instillation mode of operation.
Figure 7:
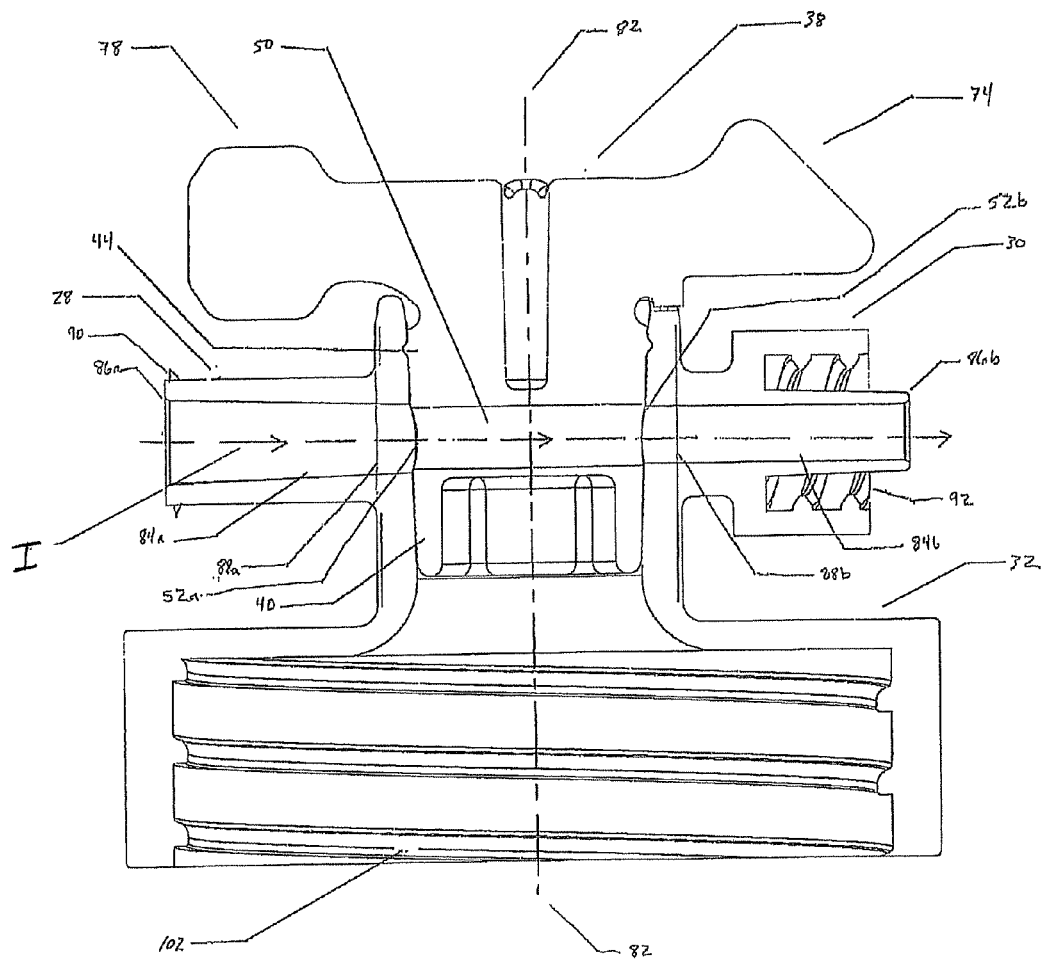
FIG. 7 is a cross-sectional view of the fluid sampling device of FIG. 6 and illustrating an instillation flow path.

In an installation position of the valve assembly 26, as illustrated in FIGS. 6 and 7, the passageway 50 of the valve body 34 is aligned with the ports 28, 30 such that the ports 28, 30 are fluidly connected to one another. A resultant inspiration fluid flow path I, represented by arrows in FIG. 7, is configured for the installation procedure. The passageway 50 is connected through the openings 72a, 72b in the housing 36 to each of the respective ports 28, 30 in order to provide a path for fluids during installation of the patient. In this position, no fluids or specimens may pass out of or into the container 24 (FIG. 1). As a point of reference, the specimen container 24 need not be connected to the fluid flow control apparatus 22 in the inspiration position or mode; however, the specimen container 24 may be connected without affecting the installation procedure. Fluid may thus be injected with a syringe or other similar apparatus, down a tube or catheter into the lungs or other body cavities/organ. In this manner, fluid flow is directly from a fluid source, through the fluid flow control apparatus 22, and into a patient or suction apparatus.

Figure 8:
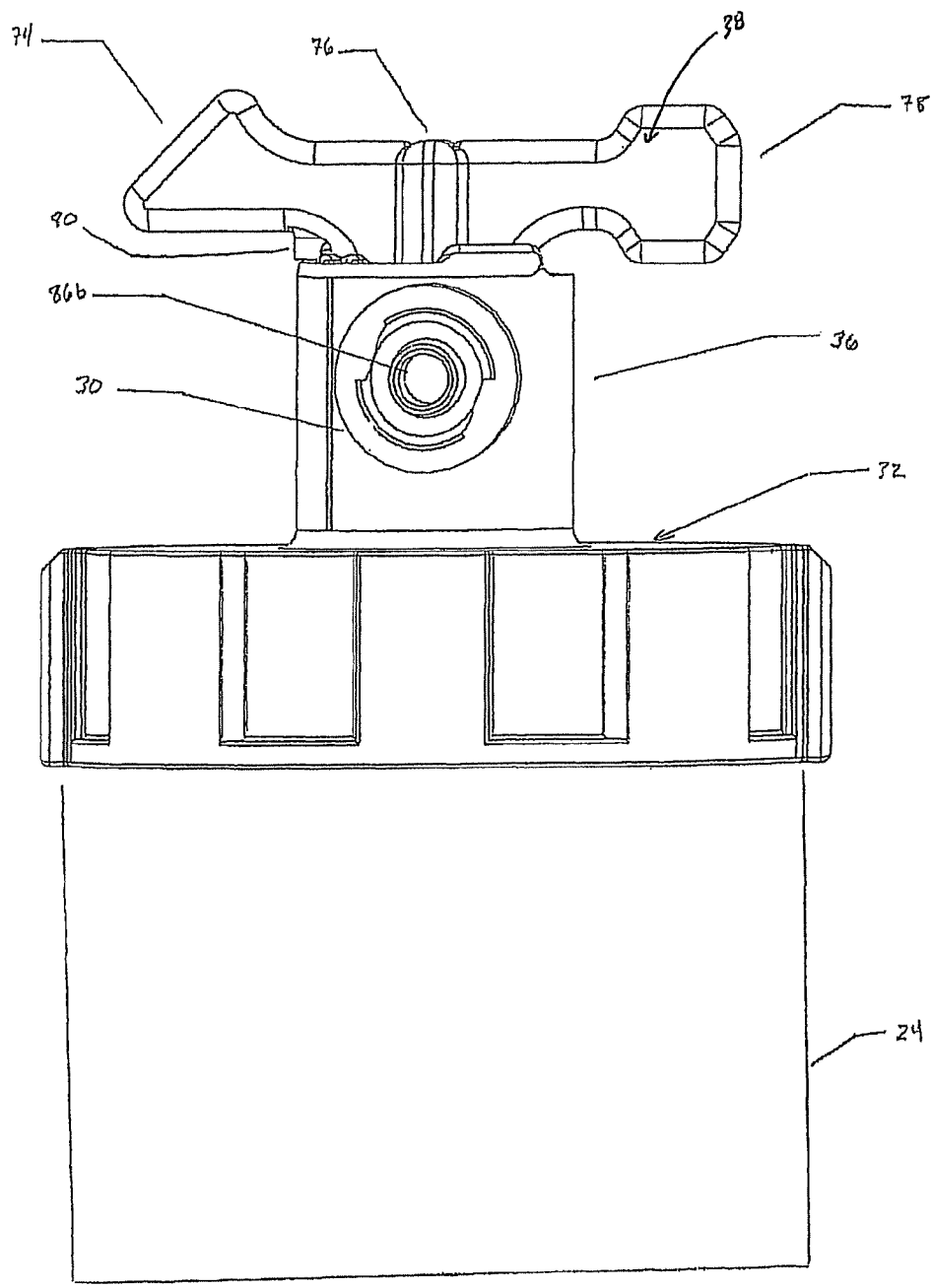
FIG. 8 is a front view of the fluid sampling device of FIG. 1 in an aspiration mode of operation.
Figure 9:
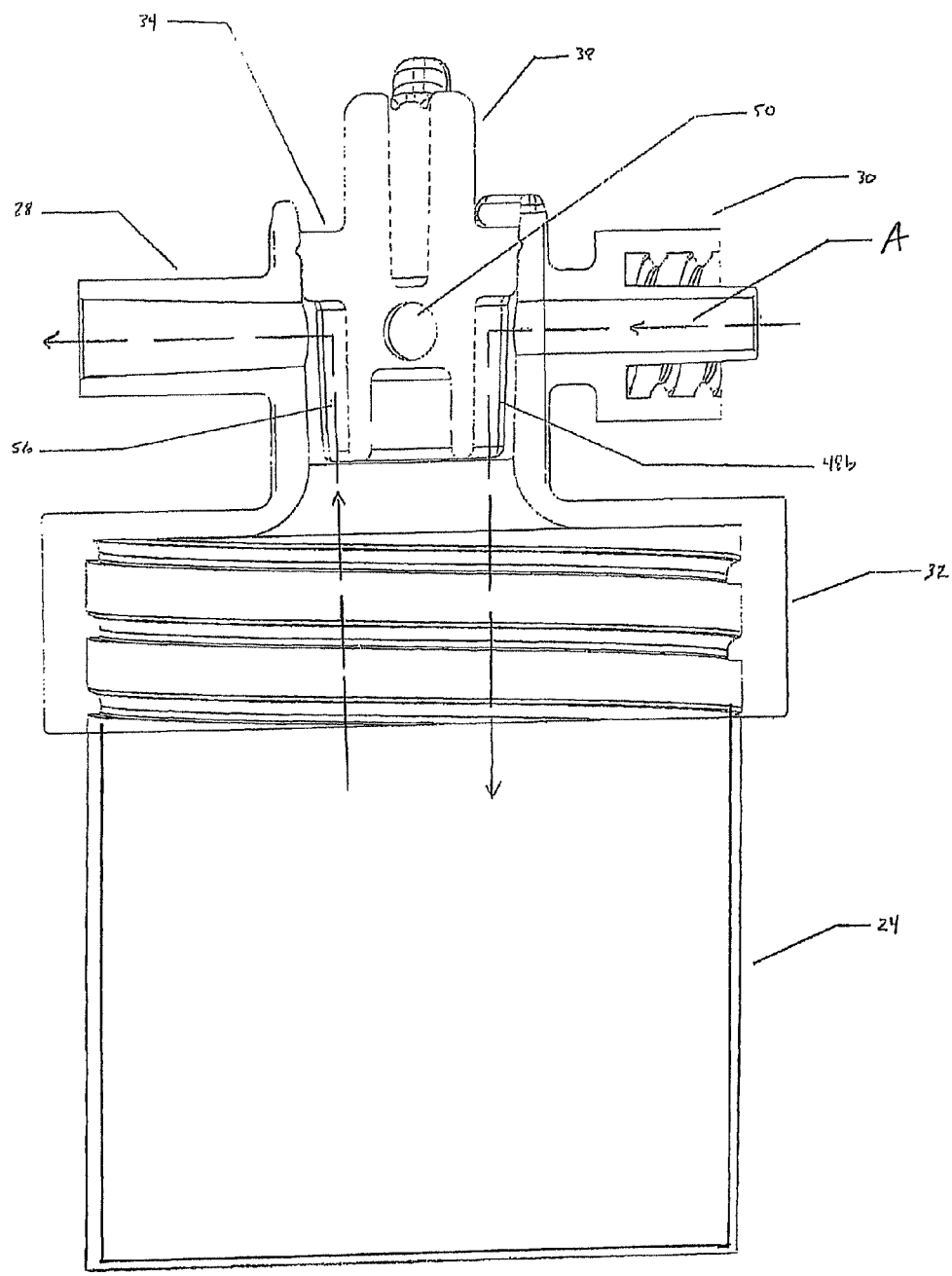
FIG. 9 is a cross-sectional view of the fluid sampling device of FIG. 8 and illustrating an aspiration flow path.
Figure 10:
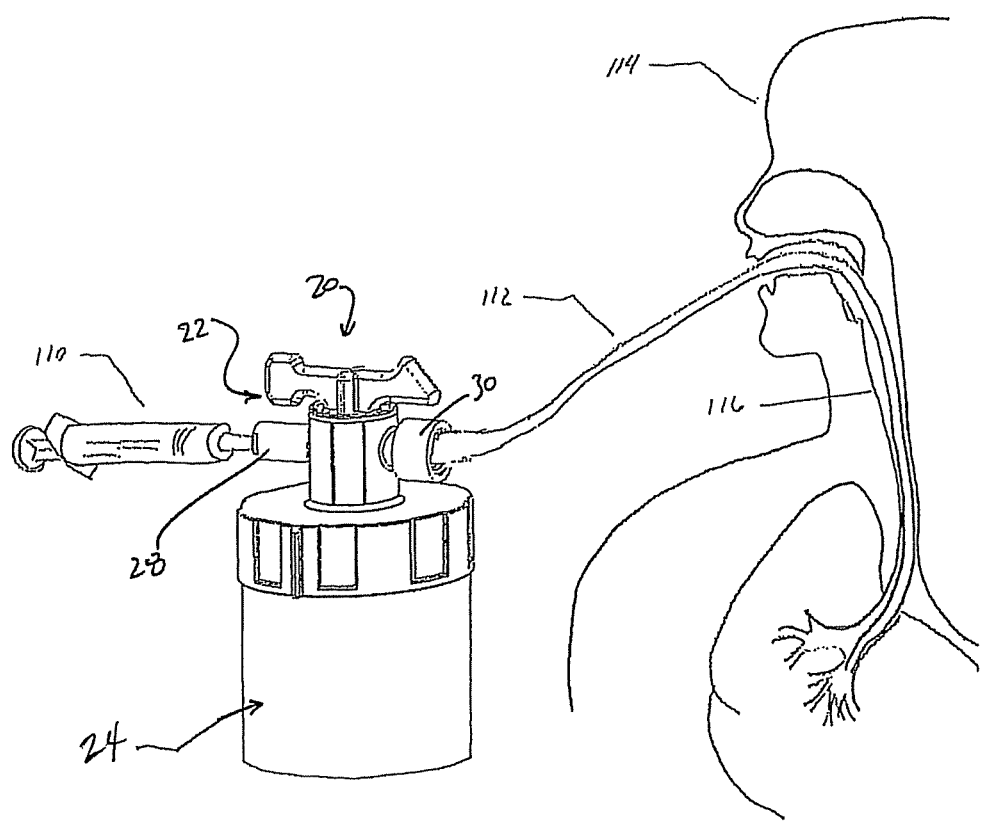
FIG. 10 illustrates use of the fluid sampling device of FIG. 1 in performing a medical specimen collection procedure.

In a second position, the first and second ports 28, 30 are fluidly connected to the specimen container 24, as illustrated in FIGS. 8 and 9. Here, the valve body 34 is oriented such that the passageway 50 is blocked by the housing 36 and does not connect to the ports 28, 30. In this position, aspiration can occur and fluid samples may be drawn into the specimen container 24 attached to the cap 32 with negative pressure by using a suction means attached to the first port 28. A resultant aspiration fluid flow path A (represented by arrows in FIG. 9) is through the second port 30, the connected recess 48b, into the specimen container 24, where the fluid is collected, and then continues out of the specimen container 24, through the opposing recess 48a, and to the first port 28 connected to a suctioning device. As further illustrated in FIG. 10, when a syringe 110 or other suction device is connected to the first port 28, fluid is drawn back through the second port 30 and into the specimen container 24 and the air flows back to the syringe 110. In another embodiment, the second port 30 is connected to tubing 112 that in turn is fluidly connected to an endotracheal tube or a tracheostomy tube; alternatively, the artificial airway 112 can be directly connected to the second port 30. The second port 26 is configured for fluid connection to the artificial airway 112 otherwise establishing a direct connection to the patient's respiratory track 116. In this manner, specimens may be collected.

A third position of the fluid flow control apparatus 22, when available, is located between the installation and aspiration positions described above. The third position is a paused position. In this position, the ports 28, 30 are blocked and pressure to the catheters 112 is maintained in order that additional fluid or vacuum can be prepared for attachment to the first port 28. In one embodiment, a fourth position is available beyond the aspiration position, whereby the ports 28, 30 are sealed (i.e., fluidly disconnected from the passageway 50 and the recesses 48a, 48b) for sending the collected specimen for analysis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A fluid flow control apparatus used in medical fluid sampling, comprising:

a valve assembly comprising a housing and a body, the housing having a cavity between a top surface and a first opening of the housing, the body having a top portion and a bottom portion, the body rotatably retained within the cavity such that the bottom portion terminates above the housing first opening and the top portion extends above the housing top surface, the body comprising a passageway through a horizontal axis of the body and defining at least two diametrically opposed circumferential recesses along respective vertical axes of the body parallel to the axis of rotation, the at least two diametrically opposed circumferential recesses defined by an interior circumferential surface of the housing and respective recessed portions of an exterior surface of the body, that are fluidly isolated from the passageway;

the housing having (i) a first port and a second port, each port extending from the housing and configured for connection to medical devices, and (ii) a ridge on the top surface of the housing comprising first and second protrusions, the first protrusion being engaged by a stem portion in a first flow position, and the body being rotatable such that the stem portion engages a second protrusion in a second flow position; and a cap integrally connected to the first opening of the housing, the cap forming a chamber for coupling to a specimen container, the chamber having cross-sectional width that is greater than the cross-sectional width of the first opening, wherein the chamber of the cap is configured to be fluidly connected to the first and second ports through the at least two diametrically opposed circumferential recesses when two of the at least two diametrically opposed circumferential recesses are aligned with the first and second ports, wherein the valve assembly is operable to interchangeably align the passageway and two of the at least two diametrically opposed circumferential recesses with the first and second ports.

2. The fluid flow control apparatus of claim 1, wherein the valve assembly comprises a stopcock valve.

3. The fluid flow control apparatus of claim 1, wherein the first port is a female fitting and the second port is a male fitting.

4. The fluid flow control apparatus of claim 1, wherein the first port and second port are luer fittings.

5. The fluid flow control apparatus of claim 1, wherein the valve assembly is configured to provide at least two flow positions.

6. The fluid flow control apparatus of claim 5, wherein the protrusion corresponds to each of the at least two flow positions of the valve assembly.

7. The fluid flow control apparatus of claim 5, wherein a first flow position of the valve assembly includes the passageway fluidly connecting the first and second ports.

8. The fluid flow control apparatus of claim 5, wherein a second flow position of the valve assembly defines a direction of fluid flow from the first port, through one of the at least two diametrically opposed circumferential recesses, into the cap, through an opposite of the at least two diametrically opposed circumferential recesses and the second port.

9. A fluid sampling apparatus for use in medical fluid sampling comprising:
   a first port;
   a second port;
   a valve assembly including four flow positions, comprising a body and a housing, the housing having a cavity between a top surface and a first opening of the housing, the body having a top portion and a bottom portion, the body rotatably retained within the cavity such that the bottom portion terminates above the housing first opening and the top portion extends above the housing top surface, the body comprising a passageway and at least two diametrically opposed circumferential recesses defined by an interior circumferential surface of the housing and respective recessed portions of an exterior surface of the body, the at least two diametrically opposed circumferential recesses being fluidly isolated from the passageway;
   a cap integrally connected to the first opening of the housing, the cap forming a chamber fluidly connected to the first and second ports through the at least two diametrically opposed circumferential recesses, the chamber having a cross-sectional width that is greater than the cross-sectional width of the first opening; and
   a fluid sampling container removably connected to the cap.

10. The fluid sampling apparatus of claim 9, wherein an instillation position of the valve assembly fluidly connects the first port to the second port.

11. The fluid sampling apparatus of claim 9, wherein the at least two diametrically opposed circumferential recesses are formed by an intersection of the body with the housing of the valve assembly, and further wherein an aspiration position of the valve assembly fluidly connects the first port and the second port to the fluid sampling container via the at least two diametrically opposed circumferential recesses.

12. The fluid sampling apparatus of claim 9, wherein the cap forms a threaded interior for removable connection to the fluid sampling container.

13. The fluid sampling apparatus of claim 9, wherein the valve assembly includes a handle coupled to the top portion of the body, the handle having a flow indicating end.

14. The fluid sampling apparatus of claim 9, further including position indicators corresponding to the four flow positions of the valve assembly.

15. A method of obtaining a fluid sample from a patient, comprising:
   inserting an artificial airway into a patient;
   connecting the artificial airway to a first port of a fluid sampling apparatus;
   the fluid sampling apparatus comprising:
   a valve assembly comprising a housing and a body, the housing having a cavity between a top surface and a first opening of the housing, the body having a top portion and a bottom portion, the body rotatably retained within the cavity such that the bottom portion terminates above the housing first opening and the top portion extending above the housing top surface, the body comprising a passageway through a horizontal axis of the body and defining at least two diametrically opposed circumferential recesses along respective vertical axes of the body parallel to the axis of rotation, the at least two diametrically opposed circumferential recesses defined by an interior circumferential surface of the housing and respective recessed portions of an exterior surface of the body, that are fluidly isolated from the passageway;
   the housing having (i) the first port and a second port, each port extending from the housing and configured for connection to medical devices, and (ii) a ridge on the to surface of the housing comprising first and second protrusions, the first protrusion being engaged by a stem portion in a first flow position, and the body being rotatable such that the stem portion engages a second protrusion in a second flow position; and
   a cap integrally connected to the first opening of the housing, the cap forming a chamber for coupling a specimen container, the chamber having a cross-sectional width that is greater than the cross-sectional width of the first opening,
   wherein the chamber of the cap is configured to be fluidly connected to the first and second ports through the at least two diametrically opposed circumferential recesses when two of the at least two diametrically opposed circumferential recesses are aligned with the first and second ports,
   wherein the valve assembly is operable to interchangeably align the passageway and two of the at least two diametrically opposed circumferential recesses with the first and second ports;
   orienting the valve assembly of the fluid sampling apparatus to provide a flow passageway from the first port to the passageway of the valve assembly to the second port;
   instilling a fluid into the fluid sampling apparatus to the patient;
   redirecting the valve assembly and the flow passageway through the specimen container; and
   aspirating a fluid sample from the patient by providing a negative pressure at the second port.

16. The method of claim 15, further comprising redirecting the valve assembly to seal the passageway and maintain internal pressure.

* * * * *